United States Patent [19]

Michel et al.

[11] 4,271,286

[45] Jun. 2, 1981

[54] PROCESS FOR THE PREPARATION OF ETHERIFIED METHYLOLAMINOTRIAZINES

[75] Inventors: Walter Michel; Hans Hönel, both of Frankfurt am Main; Manfred Schön, Dudenhofen; Wolfgang Kaiser, Hanau, all of Fed. Rep. of Germany

[73] Assignee: Cassella Aktiengesellschaft, Frankfurt am Main, Fed. Rep. of Germany

[21] Appl. No.: 136,416

[22] Filed: Apr. 2, 1980

[30] Foreign Application Priority Data

Apr. 14, 1979 [DE] Fed. Rep. of Germany ....... 2915315

[51] Int. Cl.$^3$ ............................................. C08G 12/30
[52] U.S. Cl. .................................................. 528/254
[58] Field of Search .......................................... 528/254

[56] References Cited

U.S. PATENT DOCUMENTS

| | | | |
|---|---|---|---|
| 4,039,493 | 8/1977 | Schön et al. | 528/254 X |
| 4,081,426 | 3/1978 | Michel et al. | 528/254 |

*Primary Examiner*—Lucille M. Phynes
*Attorney, Agent, or Firm*—Connolly and Hutz

[57] ABSTRACT

An improved process for the preparation of methylolaminotriazines etherified with alkanols and having per mol of the aminotriazine, an analytically determined average of 0.6 n to 2 n preferably 0.7 to 2 n methylol groups, which are etherified to the extent of 30 to 60%, n being the number of amino groups in the aminotriazine, wherein an aminotriazine is warmed to 80° to 130° C. with 0.7 n to 3 n mols of formaldehyde, 2 n to 10 n mols alkanol or a mixture of alkanols having 1 to 8 carbon atoms, the carbon chain of which, if having more than 2 carbon atoms, can also be interrupted by an oxygen atom, and 0 to 5 n mols of water, per mol of the aminotriazine, for 0.2 to 20 minutes, under elevated pressure, wherein the improvement comprises said aminotriazine being first heated to a temperature of 60°–90° C. in the presence of the formaldehyde and 0 to 30% by weight of the total amount of alkanol or alkanol mixture for 1 to 30 minutes at a pH 8 to 11 whereupon the remainder of the alkanol or alkanol mixture is added and the mixture is subsequently heated to 80° to 130° C. under elevated pressure in the presence of a strong inorganic or organic acid, at a pH of 3 to 8, for 0.2 to 20 minutes.

9 Claims, No Drawings

PROCESS FOR THE PREPARATION OF ETHERIFIED METHYLOLAMINOTRIAZINES

U.S. Pat. No. 4,081,426 relates to a process for the preparation of methylol-aminotriazines which are etherified with alkanols and have, per mol of the aminotriazine, an analytically determined average of 0.7 n to 2 n methylol groups, which are etherified to the extent of 30–60%, n being the number of amino groups in the aminotriazine, in which process an aminotriazine is reacted with formaldehyde and an alkanol or with an alkanol mixture at a pH value between 3 and 6.5, at temperatures between 80° and 130° C. and under increased pressure.

In the course of recent industrial development, etherified methylol-aminotriazines have become more and more important. They are employed in continuously increasing amounts in numerous fields of application. Thus, for example, they are indispensable as aminoplast crosslinking agents in water-soluble and solvent-soluble lacquer combinations, as crosslinking agents for latices and dispersion binders containing hydroxyl groups, for the production of moulding compositions, as constituents of water-resistant adhesives for veneer sizing, in the production of laminates, edge bands and the surface-texturing of sheet material. Methylol-aminotriazines which are etherified with alkanols, but mainly etherified with methyl are also used in the paper industry for producing surfaces of good wet and dry tear strength and for improving paper coatings, in particular for rendering them water-resistant, and in the textile industry such products are employed as high-quality finishing agents.

In the application of the methylol-aminotriazines, etherified with alkanols, in all the abovementioned fields, it is particularly desirable for the hardened coatings and surface films crosslinked with aminoplasts and formed therefrom by a hardening process brought about by the action of acid and/or heat to have the properties of surface hardness, scratch resistance, stability to dry heat, resistance to steam, adhesion and resilience.

The etherified methylol-aminotriazines are prepared by reacting the aminotriazine with formaldehyde and the alkanol used for the etherification, in the presence of an acid. The reaction has hitherto always been carried out in the temperature range between normal room temperature and the boiling point of the reaction mixture. However, this conventional process displays serious disadvantages. Firstly, the space/time yield of the process is unsatisfactory, especially if etherified methylol-aminotriazines with a low degree of methylolation are to be prepared. In that case, reaction times which make the known processes completely uneconomical are soon reached. If, in this case, attempts are made to increase the rate of reaction by increasing the acid concentration in the batches, when the reaction has ended and the acid has been neutralised the salt formed must be removed from the precondensates, for which a filtration operation is necessary, which cancels out the saving in time which has been achieved by the higher rate of reaction. This disadvantage is all the more unacceptable since resins with a low formaldehyde content, in particular, offer considerable advantages when used in the laminates sector: they exhibit a relatively high reactivity and split off substantially less formaldehyde during hardening, which means they are considerably easier to use. Another disadvantage of the known processes is that it is scarcely possible to prepare precondensates which have a low degree of methylolation and are stable on storage, that is to say which do not tend to crystallise on prolonged storage.

According to the process of U.S. Pat. No. 4,081,426, these disadvantages can be avoided if, for the preparation of methylol-aminotriazines which are etherified with alkanols and have, per mol of the aminotriazine, an analytically determined average of 0.7 n to 2 n methylol groups, which are etherified to the extent of 30 to 60%, n being the number of amino groups in the aminotriazine, an aminotriazine is warmed to 80°–130° C. with 0.7 n to 3 n mols of formaldehyde, 2 n to 10 n mols of an alkanol or a mixture of alkanols with 1–8 carbon atoms, the carbon chain of which, if it has more than 2 carbon atoms, can also be interrupted by an oxygen atom, and 0 to 5 n mols of water, per mol of the aminotriazine, in the presence of an inorganic or organic acid at a pH value between 3 and 6.5, for 0.2 to 20 minutes, under increased pressure. 0.77 n–3 n mols of formaldehyde and 2.5 n–7 n mols of the alkanol or alkanol mixture are preferably used per mol of the aminotriazine. To establish particular degrees of condensation, the amount of water added is preferably varied in the range from 0 to 3 n mols of the aminotriazine. To prepare products with a particularly low degree of condensation, the reaction is preferably carried out under anhydrous conditions. Aminotriazines which can advantageously be reacted by this process are benzoguanamines and, in particular, melamine.

It has now been found that products with properties which have been improved further, in particular further enhanced compatibility with organic binders and diluents, lower viscosity and outstanding reactivity, coupled with further enhanced storage stability in the presence of crosslinkable binders, and having per mol of aminotriazine an analytically determined average of 0.6 to 2 n, preferably 0.7 to 2 n methylol groups, are obtained if the aminotriazine is first warmed with the formaldehyde and with 0 to 30% by weight of the envisaged amount to alkanol or alkanol mixture to temperatures of 60°–90° C., preferably of 70°–80° C., for 1 to 30 minutes, preferably 10–20 minutes, at pH values of 8 to 11, preferably of 9–10.5, the ramainder of the envisaged amount of alkanol or alkanol mixture is then added and the mixture is subsequently warmed to 80° to 130° C. under increased pressure at a pH value between 3 and 8, preferably between 3 and 7 for 0.2 to 20 minutes.

Examples of alkanols which are suitable for use in the process according to the invention are: methanol, ethanol, propanol, n-butanol, butan-2-ol, isobutanol, pentan-1-ol, pentan-2-ol, pentan-3-ol, methylbutanol, hexanol, isohexanol, methylhexanol, ethylhexanol, benzyl alcohol and 2-phenylethanol. Alkanols, the carbon chain of which is interrupted by an oxygen atom are, for example: methoxyethanol, ethoxyethanol, propoxyethanol, methoxypropanol, methoxyisopropanol, ethoxypropanol, methoxy- or ethoxy-butanol and methoxy- or ethoxy-isobutanol. Preferred alkanols are those which contain 1 to 4 carbon atoms, the carbon chain of which, if it has more than 2 carbon atoms, can likewise be interrupted by an oxygen atom.

The use of alkanol mixtures leads to the formation of mixed etherified methylol-aminotriazines.

It is particularly preferable to use methanol as the alkanol, or to use an alkanol mixture containing at least 40 mol % of methanol.

The new procedure also permits an increase in the scope for varying the particular, advantageous properties of the process products, and thus an additional extension of their advantageous possible uses, if alkanols or alkanol mixtures which contain 15 to 20% by weight of a glycol with 2 to 4, preferably 2 to 3, C atoms, or of a polyethylene glycol with 2 to 4, preferably 2 or 3, ethylene glycol units, and monoalkyl($C_1$–$C_4$) ethers thereof, are employed. Diols with 1 to 4 C atoms and polyethylene glycols and monoalkyl ethers thereof which can be used for the process according to the invention are ethylene glycol; 1,2- and 1,3-propanediol; 1,2-, 1,3- or 1,4-butanediol, diethylene glycol (HO—$CH_2CH_2$O—$CH_2CH_2$—OH), triethylene glycol H(O$CH_2CH_2$—)$_3$—OH and tetraethylene glycol H(O$CH_2CH_2$)$_4$—OH, glycol monomethyl, monoethyl, monopropyl or monobutyl ether, diethylene glycol monomethyl, monoethyl, monopropyl or monobutyl ether, and triethylene glycol monobutyl ether. Ethylene glycol, the propanediol and di- and tri-ethylene glycol are preferred.

After adding the entire alkanol or alkanol mixture, etherification of the methylol-aminotriazines formed in the first reaction step carried out under normal pressure takes place. The preferred temperature range for this etherification is between 85° and 115° C. Since the boiling point of the etherification mixture is in general below 90° C. under normal pressure, the reaction is carried out in an apparatus which is sealed pressure-tight. In the case where the boiling point of the reaction mixture is above 80° C., preferably above 90° C., under normal pressure when higher alkanols are used, the temperature is increased to the extent such that an excess pressure of at least 0.1 atmosphere is established in the apparatus. The etherification with the entire amount of the alkanol or alkanol mixture is carried out at pH values between 3 and 8, preferably 3 and 7, most preferably 6 and 7.0. This pH value can be achieved by adding a strong inorganic or organic acid to the reaction batch in amount of about 0.1 to 1 part per thousand. Acids which can be employed for the process according to the invention are inorganic acids, such as, for example, sulphuric acid, nitric acid, hydrobromic acid, hydrochloric acid, hydrofluoric acid or hydroiodic acid, and compounds from which these acids are liberated under the reaction conditions claimed, or organic acids of comparable acid strength, such as, for example, sulphonic acids, formic acid or halogenoacetic acids.

In principle, there is also the possibility of establishing the necessary pH value by adding weaker acids, but it is advantageous to carry out the reaction with stronger acids.

If appropriate, the process according to the invention can also be carried out in the presence of inert organic solvents. Examples of suitable inert organic solvents are: lower aromatics, aliphatic ethers, substituted amides, such as dimethylformamide, and tertiary alcohols, such as tertiary butanol.

The process according to the invention combines the advantages of the process of U.S. Pat. No. 4,081,426 with a still further improved quality of the process products in respect of compatibility with organic binders and diluents, which makes it possible to use the products in even more strongly oleophilic binder systems, of lower viscosity and of higher reactivity, coupled at the same time with a long shelf life, even in the presence of crosslinkable binders. The process is even more flexible and the properties of the products can hence be even better matched to practical requirements. Thus, products with a further enhanced self-crosslinkability and which are outstandingly suitable as sole binders, for example for the production of bonded random fibre webs, can be obtained.

The percentage data in the examples which follow are percentages by weight. The solids content indicated in the examples is determined by drying a sample of about 2 g of solution at 120° C. for 1 hour and determining the residue. The flow times given for the viscosity data in the examples are flow times measured in accordance with the method of 4/DIN 53 211, that is to say they were determined by means of DIN flow cups according to DIN 53 211.

The comparison examples illustrate resins with a composition (in respect of the starting materials) which is the same as or very closely related to that of the example concerned, but which are prepared by the process of U.S. Pat. No. 4,081,426.

EXAMPLE 1

2,400 g of melamine, 5,860 g of 39% strength aqueous formaldehyde solution and 10 g of 50% strength sodium hydroxide are warmed to 75° C. in a vessel, which can be sealed pressure-tight, with the pressure seal open and using a reflux condenser, and the mixture is stirred at this temperature for 15 minutes. The initially undissolved melamine dissolves completely in the course of the reaction.

The clear solution is cooled to 45° to 40° C. and 10,440 g of methanol and 11 g of 65% strength nitric acid are added, whereupon the pH value drops to 6.5.

The reaction vessel is now sealed pressure-tight and warmed to 85°–87° C. and the mixture is stirred at this temperature for 15 minutes, whereby an internal pressure of 1.5 bars is established.

A pH value of 9.5 is then again established by adding 13 ml of 27% strength sodium hydroxide and the mixture is evaporated at 70° C. under reduced pressure, to a solids content of 75% by weight.

A clear resin solution with a viscosity of 101 DIN seconds, determined at 20° C. in a 4 mm flow cup in accordance with the method of DIN 53 211, is obtained. Miscibility with water: 1:00; miscibility with isopropanol: 1:3.

Cooling of the batch before addition of the 10,440 g of methanol can be omitted if the methanol is added not too rapidly, through the reflux condenser.

COMPARISON EXAMPLE 1a 5,150 g of methanol, 2,930 g of 39% strength aqueous formaldehyde solution, 6 ml of concentrated nitric acid and 1,200 g of melamine are mixed in an autoclave. The pH value of the mixture is 5.5. After sealing the vessel pressure-tight, it is warmed to 90° C. in the course of 5 minutes, whilst stirring, whereby a pressure of 1.7 to 1.8 bars is established. Stirring is continued at this temperature for 15 minutes. When this time has elapsed, 15 ml of 27% strength sodium hydroxide solution are injected in and the autoclave is cooled immediately. The reaction product is then concentrated to a solids content of 75% by weight by evaporation under about 30 mbars and at 70° C. A clear resin solution with a viscosity of 255 DIN seconds, determined in a 4 mm flow cup in accordance with the method of DIN 53 211, is obtained. Miscibility with water: 1:2; miscibility with isopropanol: 1:2.3.

EXAMPLE 2

1,260 g of melamine, 5,390 g of 39% strength aqueous formaldehyde solution and 60 g of 50% strength sodium hydroxide are warmed to 75° C. in a vessel, which can be sealed pressure-tight, with the pressure seal open and using a reflux condenser, and the mixture is stirred vigorously at this temperature for 15 minutes, the initially undissolved melamine dissolving completely in the course of the reaction; towards the end of the reaction, a precipitate of methylolmelamine separates out. The suspension is cooled to 45° to 40° C. and 5,400 g of methanol and 31 ml of 65% strength nitric acid are added, whereupon the pH value drops to 6.6.

The reaction vessel is now sealed pressure-tight and warmed to 85°-87° C. and the mixture is stirred at this temperature for 15 minutes, whereby an internal pressure of 1.4 bars is established.

A pH value of 10 is then again established by adding 10 ml of 27% strength sodium hydroxide solution and the mixture is evaporated at 70° C. under reduced pressure, to a solids content of 73.5% by weight.

A clear resin solution with a viscosity of 90 DIN seconds, determined at 20° C. in a 4 mm flow cup in accordance with the method of DIN 53 211, is obtained. Miscibility with water: 1:∞; miscibility with isopropanol: 1:∞.

Cooling of the batch before the addition of the 5,400 g of methanol can be omitted if the methanol is added not too rapidly, through the reflux condenser.

COMPARISON EXAMPLE 2a 1,500 g of methanol, 1,325 g of 39% strength aqueous formaldehyde solution, 316 g of melamine and 2 g of p-toluene-sulphonic acid, dissolved in 25 g of methanol, are mixed in an autoclave. After sealing the vessel pressure-tight, it is warmed to 90° C., whilst stirring, whereby a pressure of 1.5 bars is established. Stirring is continued at this temperature for 5 minutes. After this time has elapsed, 35 ml of 10% strength sodium bicarbonate solution are injected in and the autoclave is cooled immediately. The reaction product is then concentrated to a solids content of 75% by weight by evaporation under about 30 mbars and at 70° C.

After cooling, the concentrated solution solidifies. In contrast to the resin solution prepared according to Example 2, it can thus no longer be processed at room temperature.

EXAMPLE 3

63.0 kg of melamine, 204 kg of 39% strength aqueous formaldehyde solution, 45 kg of methanol and 343 g of 50% strength sodium hydroxide solution are warmed to 75° C. in a vessel, which can be sealed pressure-tight, with the pressure seal open and using a reflux condenser, and the mixture is stirred vigorously at 75° to 65° C. for 10 minutes. The initially undissolved melamine dissolves completely in the course of the reaction, and methylolmelamine separates out of the solution as a white solid.

The suspension is cooled to 45° to 40° C. and 280 kg of methanol and 350 ml of 65% strength nitric acid are added, whereupon the pH value drops to 6.5.

The reaction vessel is now sealed pressure-tight and warmed to 85°-87° C. and the mixture is stirred at this temperature for 15 minutes, whereby an internal pressure of 0.85 bar is established.

A pH value of 10.5 is then again established by adding 400 ml of 27% strength sodium hydroxide and the mixture is evaporated at 70° C. under reduced pressure, to a solids content of 75% by weight.

A clear resin solution with a viscosity of 116 DIN seconds, determined at 20° C. in a 4 mm flow cup in accordance with the method of DIN 53 211, is obtained. Miscibility with water: 1:∞; miscibility with isopropanol: 1:∞.

Cooling of the batch before the addition of the 280 kg of methanol can be omitted if the methanol is added not too rapidly, through the reflux condenser.

COMPARISON EXAMPLE 3a 6,825 g of methanol, 4,284 g of 39% strength aqueous formaldehyde solution, 1.4 g of concentrated nitric acid and 1,323 g of melamine are mixed in an autoclave. The pH value of the mixture is 6.2. After sealing the vessel pressure-tight, it is warmed to 80° C., whilst stirring, whereby a pressure of 1.0 bar is established. Stirring is continued at this temperature for 35 minutes. After this time has elapsed, 2 ml of 27% strength sodium hydroxide solution are injected in and the autoclave is cooled immediately. The reaction product is then concentrated to a solids content of 75% by weight by evaporation under about 30 mbars and at 70° C.

After cooling, the concentrated solution solidifies. In contrast to the resin solution prepared according to Example 1, it can thus no longer be processed at room temperature. However, on warming to 80° C., a clear solution with a viscosity of 230 DIN seconds in a 4 mm flow cup, and with a miscibility with water of 1:∞ and a miscibility with isopropanol of 1:∞ is obtained.

EXAMPLE 4

63 kg of melamine, 216 kg of 39% strength aqueous formaldehyde solution, 92 kg of methanol and 390 g of 50% strength sodium hydroxide are warmed to 75° C. in a vessel, which can be sealed pressure-tight, with the pressure seal open and using a reflux condenser and the mixture is stirred at this temperature for 15 minutes. The initially undissolved melamine dissolves completely in the course of the reaction.

The clear solution is cooled to 45° to 40° C., whereupon a precipitate of methylolmelamine separates out, and 217 kg of methanol and 1.5 l of 65% strength nitric acid are added.

The reaction vessel is now sealed pressure-tight and warmed to 85°-87° C. and the mixture is stirred at this temperature for 15 minutes, whereby an internal pressure of b 0.9 bar is established.

A pH value of 10-is then again established by adding about 800 ml of 27% strength sodium hydroxide solution and the mixture is evaporated at 70° C. under reduced pressure, to a solids content of 74% by weight.

A clear resin solution with a viscosity of 118 DIN seconds, determined at 20° C. in a 4 mm flow cup in accordance with the method of DIN 53 211, is obtained. Miscibility with water: 1:∞; miscibility with isopropanol: 1:∞.

COMPARISON EXAMPLE 4a 1,500 g of methanol, 1,156 g of 39% strength aqueous formaldehyde solution, 316 g of melamine and 1 g of p-toluenesulphonic acid, dissolved in 25 ml of methanol, are mixed in an autoclave. After sealing the vessel pressure-tight, it is warmed to 100° C., whilst stirring, whereby a pressure of 1.7 bars is established. Stirring is continued at this temperature for 9 minutes. After this time has elapsed, 10 ml of 10% strength sodium bicarbonate solution are injected in and the autoclave is cooled immediately. The reaction product is then concentrated to a solids content of 75% by weight by evaporation under about 30 mbars and at 70° C.

The clear resin solution thus obtained has a viscosity of 210 DIN seconds in a 4 mm flow cup at 20° C., coupled with unlimited miscibility in water and isopropanol.

EXAMPLE 5

1,260 g of melamine, 3,846 g of 39% strength aqueous formaldehyde solution, 900 g of methanol and 6 g of 50% strength sodium hydroxide are warmed to 75° C. in a vessel, which can be sealed pressure-tight, with the pressure seal open and using a reflux condenser, and the mixture is stirred at this temperature for 10 minutes. The mixture has a pH value of 10, and the initially undissolved melamine dissolves completely in the course of the reaction.

The clear solution is cooled to 45° to 40° C. and 5,266 g of methanol, 468 g of triethylene glycol and 45 g of 65% strength nitric acid are added, whereupon the pH value drops to 6.5. The reaction vessel is now sealed pressure-tight and warmed to 85°–87° C. and the mixture is stirred at this temperature for 15 minutes, whereby an internal pressure of 1.5 bars is established. A pH value of 10 is then again established by adding 6.5 g of 55% strength sodium hydroxide and the mixture is evaporated at 70° C. under reduced pressure, to a solids content of 75% by weight. A clear resin solution with a viscosity of 95 DIN seconds, determined at 20° C. in a 4 mm flow cup in accordance with the method of DIN 53 211, is obtained. Miscibility with water: 1:∞; miscibility with isopropanol: 1:∞. Cooling of the batch before the addition of the 5,266 g of methanol can be omitted if the methanol is added not too rapidly, through the reflux condenser.

If the addition of the 468 g of triethylene glycol before the etherification is omitted, a product which has a significantly reduced miscibility with isopropanol but otherwise virtually identical properties is obtained.

COMPARISON EXAMPLE 5a 4,362 g of methanol, 2,740 g of 39% strength aqueous formaldehyde solution, 8.8 g of 27% strength sodium hydroxide solution, 330 g of triethylene glycol and 900 g of melamine are mixed in an autoclave. The pH value of the mixture is 11. After sealing the vessel pressure-tight, it is warmed to 85° to 87° C., whilst stirring, whereby a pressure of 1.2 bars is established. 6.6 g of 55% strength nitric acid are injected in at this temperature and stirring is continued for 10 minutes. After this time has elapsed, 10 g of 50% strength sodium hydroxide solution are injected in and the autoclave is cooled immediately. The reaction product is then concentrated to a solids content of 75% by weight by evaporation under about 30 mbars and at 70° C. After cooling, the concentrated solution solidifies. In contrast to the resin solution prepared according to Example 1, it can thus no longer be processed at room temperature.

A substance with the same properties is obtained if the amount of formaldehyde is reduced to 2,200 g.

We claim:

1. In the process for the preparation of methylolaminotriazines etherified with alkanols and having per mol of the aminotriazine, an analytically determined average of 0.6 n to 2 n methylol groups, which are etherified to the extent of 30 to 60%, n being the number of amino groups in the aminotriazine, wherein an aminotriazine is warmed to 80° to 130° C. with 0.7 n to 3 n mols of formaldehyde, 2 n to 10 n mols of an alkanol or a mixture of alkanols having 1 to 8 carbon atoms, the carbon chain of which, if having more than 2 carbon atoms, can also be interrupted by an oxygen atom, and 0 to 5 n mols of water, per mol of the aminotriazine for 0.2 to 20 minutes, under elevated pressure, wherein the improvement comprises said aminotriazine being first heated to a temperature of 60°–90° C. in the presence of the formaldehyde and 0 to 30% by weight of the total amount of alkanol or alkanol mixture for 1 to 30 minutes at a pH 8 to 11 whereupon the remainder of the alkanol or alkanol mixture is added and the mixture is subsequently heated to 80° to 130° C. under elevated pressure at a pH of 3 to 8, for 0.2 to 20 minutes.

2. The process of claim 1, wherein the mixture is heated under elevated pressure in the presence of a strong inorganic or organic acid at a pH of 3 to 7 for 0.2 to 20 minutes.

3. The process according to claim 1, wherein the alkanol or mixture of alkanols have 1 to 4 carbon atoms or an alkyl carbon chain of 2 to 4 carbon atoms interrupted by an oxygen atom.

4. The process according to claim 1 where the alkanol or mixture of alkanols is methanol or an alkanol mixture containing at least 40 mol % methanol.

5. The process according to claim 4, wherein the alkanol is methanol.

6. The process according to claim 1 wherein the alkanol or alkanol mixture contains 15 to 20% by weight of a glycol with 2 to 4 carbon atoms, a polyethylene glycol with 2 to 4 ethylene glycol units, or a monoalkyl-($C_1$–$C_4$) ether of the aforesaid glycol or polyglycol.

7. The process according to claim 1 wherein after the entire amount of alkanol or alkanol mixture has been added to the reaction, the mixture is warmed to 85° to 115° C. under pressure.

8. The process according to claim 7 wherein after the entire amount of alkanol or alkanol mixture has been added to the reaction, the reaction is carried out under a pressure of at least 0.1 atmosphere over atmospheric.

9. The process according to claim 8 wherein after adding the entire amount of alkanol or alkanol mixture, the reaction is carried out at a pH of 6 to 7.

* * * * *